United States Patent [19]

Drabek

[11] Patent Number: 4,910,018

[45] Date of Patent: Mar. 20, 1990

[54] N-BENZOYL-N'-2,4-DIFLUORO-3,5-DIHALOPHENYLUREAS, THEIR PREPARATION AND USE IN PEST CONTROL

[75] Inventor: Jozef Drabek, Oberwil, Switzerland

[73] Assignee: Ciba-Geigy Corp., Ardsley, N.Y.

[21] Appl. No.: 244,182

[22] Filed: Sep. 14, 1988

[30] Foreign Application Priority Data

Sep. 25, 1987 [CH] Switzerland ............... 3715/87
Jul. 21, 1988 [CH] Switzerland ............... 2793/88

[51] Int. Cl.⁴ ........................... A01N 25/00
[52] U.S. Cl. .................... 424/405; 514/269; 514/594
[58] Field of Search .......... 424/405; 514/594, 269; 568/927; 564/305, 306

[56] References Cited

U.S. PATENT DOCUMENTS

| | | | |
|---|---|---|---|
| 4,307,098 | 12/1981 | Fox et al. ............... | 514/269 |
| 4,310,548 | 1/1982 | Ehrenfreund . | |
| 4,404,402 | 9/1983 | Ladner et al. ........... | 564/305 |
| 4,457,943 | 7/1984 | Becher et al. . | |
| 4,713,396 | 12/1987 | Ikura et al. ............. | 514/594 |

FOREIGN PATENT DOCUMENTS

| | | |
|---|---|---|
| 0035084 | 9/1981 | European Pat. Off. . |
| 0197280 | 10/1986 | European Pat. Off. . |
| 0255678 | 2/1988 | European Pat. Off. . |
| 2123236 | 5/1970 | Fed. Rep. of Germany . |
| 3607298 | 9/1986 | Fed. Rep. of Germany . |
| 870642 | 9/1987 | South Africa . |

OTHER PUBLICATIONS

Morrison and Boyd, p. 820–Organic Chemistry.

Primary Examiner—Ellis P. Robinson
Assistant Examiner—P. L. Prater
Attorney, Agent, or Firm—Kevin T. Mansfield; Edward McC. Roberts

[57] ABSTRACT

Novel substituted N-benzoyl-N'-2,4-difluoro-3,5-dihalophenylureas of formula I

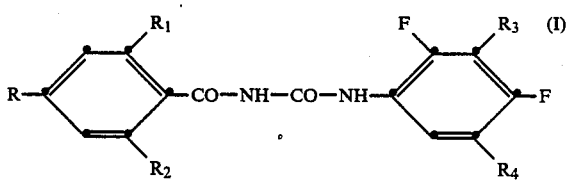

wherein R is hydrogen or fluorine; $R_1$ is hydrogen, fluorine, chlorine or methoxy; $R_2$ is fluorine, chlorine or methoxy; $R_3$ is bromine and $R_4$ is chlorine or bromine; or $R_3$ is chlorine and $R_4$ is bromine, processes and intermediates for their preparation, their use in pest control, and pesticides that contain a compound of formula I as active ingredient, are disclosed. The preferred field of application is the control of pests on animals and plants.

11 Claims, No Drawings

N-BENZOYL-N'-2,4-DIFLUORO-3,5-DIHALO-PHENYLUREAS, THEIR PREPARATION AND USE IN PEST CONTROL

The present invention relates to novel substituted N-benzoyl-N'-2,4-difluoro-3,5-dihalophenylureas, to processes and intermediates for their preparation, to pesticides that contain those compounds, and to their use in pest control.

The compounds according to the invention correspond to formula I

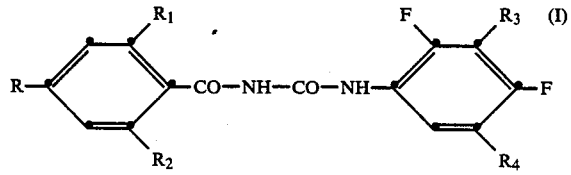

wherein R is hydrogen or fluorine; $R_1$ is hydrogen, fluorine, chlorine or methoxy; $R_2$ is fluorine, chlorine or methoxy; $R_3$ is bromine and $R_4$ is chlorine or bromine; or $R_3$ is chlorine and $R_4$ is bromine.

Prominence is given to those compounds of formula I in which R is hydrogen; $R_1$ is hydrogen, fluorine or chlorine; $R_2$ is fluorine or chlorine; $R_3$ is bromine and $R_4$ is chlorine or bromine; or $R_3$ is chlorine and $R_4$ is bromine.

Preferred compounds of formula I are those in which R is hydrogen; $R_1$ is hydrogen or fluorine; $R_2$ is fluorine or chlorine; $R_3$ is bromine and $R_4$ is chlorine; or $R_3$ is chlorine and $R_4$ is bromine.

The compounds according to the invention can be prepared according to processes known per se. Such processes are described inter alia in DE-OS 21 23 236, 26 01 780 and 32 40 975. Thus, the compounds of formula I can be obtained, for example, by (a) reacting an aniline of formula II

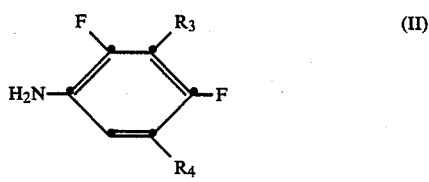

with a benzoyl isocyanate of formula III

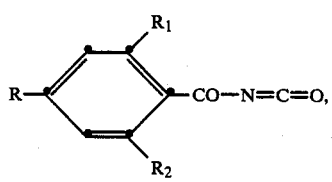

or (b) reacting an isocyanate of formula IV

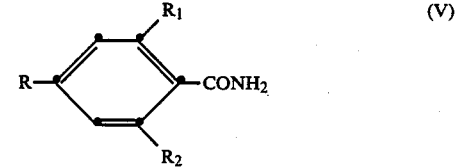

with a benzamide of formula V

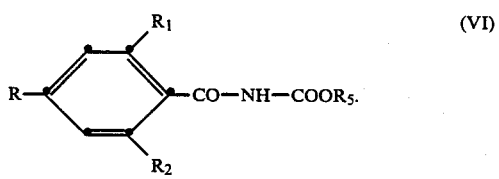

or (c) reacting an aniline of formula II with a urethane of formula VI

R—[benzene with $R_1$, $R_2$]—CO—NH—COOR$_5$.    (VI)

In formulae II, III, IV, V and VI, R, $R_1$, $R_2$, $R_3$ and $R_4$ have the meanings given for formula I and $R_5$ is a $C_1$–$C_8$alkyl radical which may be substituted by halogen, preferably chlorine.

The mentioned processes (a), (b) and (c) can preferably be carried out under normal pressure and in the presence of an organic solvent or diluent. Suitable solvents and diluents are, for example, ethers and ethereal compounds, such as diethyl ether, dipropyl ether, dibutyl ether, dioxane, dimethoxyethane and tetrahydrofuran; N,N-dialkylated carboxylic acid amides; aliphatic, aromatic and halogenated hydrocarbons, especially benzene, toluene, xylenes, chloroform, methylene chloride, carbon tetrachloride and chlorobenzene; nitriles, such as acetonitrile or propionitrile; dimethyl sulfoxide and ketones, for example acetone, methyl ethyl ketone, methyl isopropyl ketone and methyl isobutyl ketone. Process (a) is generally carried out at a temperature of from −10° to +200° C., preferably from 0° to +100° C., for example at room temperature, optionally in the presence of an organic base, for example triethylamine. Process (b) is carried out at a temperature of from 0° to +150° C., preferably at the boiling point of the solvent used, and optionally in the presence of an organic base, such as pyridine, and/or with the addition of an alkali metal or alkaline earth metal, preferably sodium. Preferred temperatures for process (c), that is to say for the reaction of the urethanes of formula VI with an aniline of formula II, are from approximately +60° C. to the boiling point of the reaction mixture, there being used as solvents especially aromatic hydrocarbons, such as toluene, xylenes, chlorobenzene etc.

The starting materials of formulae III to VI are known or can be prepared analogously to known methods.

The starting materials of formula II are novel compounds, and the present invention relates also to these.

The compounds of formula II can be prepared in a manner known per se, for example by catalytic hydrogenation of the nitrobenzene of formula VII

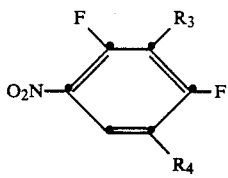
(VII)

wherein $R_3$ and $R_4$ have the meanings given for formula I. Suitable catalysts are the customary hydrogenation catalysts, for example platinum, palladium, rhenium, rhenium oxides or Raney nickel (see J. org. Chem. 29, 1964). The conversion of the $NO_2$ group into the $NH_2$ group may also be carried out by customary chemical reduction, for example with iron or tin chloride in a hydrochloric acid medium.

The nitrobenzenes of formula VII are novel, and the present invention relates also to these. They can be prepared according to a process that is known in principle by, for example, bromination of a nitrobenzene of formula VIIIa–VIIIc

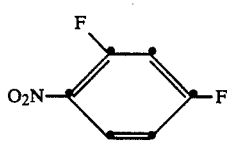
(VIIIa)

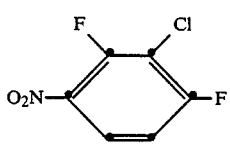
(VIIIb)

or

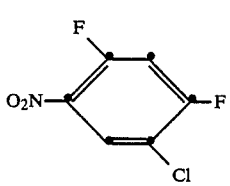
(VIIIc)

in customary manner with elementary bromine, optionally in the presence of a catalyst, for example $FeCl_3$, at from $+70°$ to $200°$ C., preferably from $+100°$ to $170°$ C., and optionally in a solvent, for example a perhalogenated hydrocarbon.

The nitrobenzenes of formulae VIIIa to VIIIc are known and can be prepared according to processes that are known in principle.

Published European Patent Application No. 0 052 833 describes, inter alia, N-halobenzoyl-N'-(2,4-difluoro-3,5-dichlorophenyl)-ureas as insecticides having larvicidal action.

Surprisingly, it has been found that the compounds of formula I according to the invention are more powerful active ingredients in pest control, while being well tolerated by warm-blooded animals and plants. Thus, the compounds of formula I are suitable, for example, for controlling pests on animals and plants. Such pests belong mainly to the arthroped family, such as, especially, insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera, and arachnids of the order Acarina, for example mites and ticks. It is possible to control every stage of development of the pests, that is to say adults, pupae and nymphs and also, especially, larvae and eggs. For example, larvae and eggs, especially, of pyrto-pathogenic insects and mites can be controlled effectively in ornamental crops and crops of useful plants, for example in fruit and vegetable crops, and especially in cotton crops. If compounds of formula I are ingested by imagines, their action may manifest itself in the immediate death of the pests or in the production of fewer eggs and/or in a reduced hatching rate. The latter phenomenon can be observed especially in the case of Coleoptera. Parasitic pests of animals, especially of pets and productive livestock, that are to be controlled are especially ectoparasites, for example mites and ticks, and Diptera, for example *Lucilia sericata*.

The compounds according to the invention are distinguished especially by excellent larvicidal activity in the case of *Spodoptera littoralis* and, especially, *Heliothis virescens*.

The good pesticidal action of the compounds of formula I according to the invention corresponds to a mortality of at least 50 to 60% of the mentioned pests.

The activity of the compounds of the invention and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formula I are used in unmodified form or, preferably, together with the inert adjuvants that are tolerated by plants and are conventionally employed in the art of formulation, and can therefore be formulated in known manner e.g. into emulsifiable concentrates, directly sprayable or dilutable solutions, dilute emulsions, wettable powders, soluble powders, dusts, granulates, and also encapsulations in e.g. polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures containing a compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of granulated materials of inorganic or organic nature can be used, e.g. especially dolomite or pulverised plant residues.

Suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid or of natural fatty acid mixtures which can be obtained e.g. from coconut oil or tall oil. Mention may also be made of fatty acid methyltaurin salts and modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$-alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily empolyed in the art of formulation are described e.g. in the following publications:

"McCutcheon's Detergents and Emulsifiers Annual" MC Publishing Corp., Ridgewood, N.J., 1979;

Dr. Helmut Stache "Tensid Taschenbuch", Carl Hanser Verlag, Munich/Vienna 1981.

The pesticidal compositions usually contain 0.1 to 99%, preferably 0.1 to 95%, of a compound of formula I or combinations thereof with other insecticides or acaricides, 1 to 99.9% of a solid or liquid adjuvant, and 0 to 25%, preferably 0.1 to 20%, of a surfactant. Whereas commercial products will preferably be formulated as concentrates, the end user will normally employ dilute formulations which contain considerably smaller concentrations of active ingredient.

The compositions may also contain further auxiliaries such as stabilisers, antifoams, viscosity regulators, binders, tackifiers as well as fertilisers or other active ingredients for obtaining special effects.

EXAMPLE 1

Preparation

1.1. Intermediates

1.1.1. Nitrobenzenes

1.1.1.1. 2,4-difluoro-3-chloro-5-bromonitrobenzene 19.2 g of 2,4-difluoro-3-chloronitrobenzene and 3 g of anhydrous FeCl$_3$ are heated to +140° C., 5.1 ml of bromine are added dropwise with stirring, and the mixture is stirred for a further 48 hours at that temperature. The reaction mixture is cooled and is then taken up in dichloromethane and washed with water. The organic phase is separated off, dried over sodium sulfate and concentrated. The residue is purified on a silica gel column using hexane/dichloromethane (10:1) as eluant. The title compound of formula

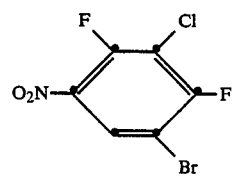

(Comp. no. 1.1.1.1.)

is obtained in the form of a brown oil; refractive index $n_D^{25}$: 1.5720.

The following compounds are prepared in an analogous manner:

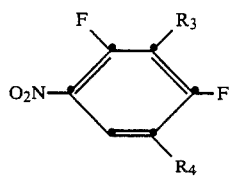

| Comp. no. | R$_3$ | R$_4$ | Physical data |
|---|---|---|---|
| 1.1.1.2. | Br | Cl | |
| | Br | Br | |

1.1.2. Anilines

1.1.2.1. 2,4-difluoro-3-chloro-5-bromoaniline 7.6 g of 2,4-difluoro-3-chloro-5-bromonitrobenzene are dissolved in 80 ml of tetrahydrofuran and hydrogenated at from +20° to 25° C. over a period of 4 hours in the presence of 1.7 g of 5% rhenium-on-carbon (hydrogen absorbed: 1.88 l). The reaction mixture is filtered, the solvent is removed by distillation, and the residue is suspended in hexane and filtered off with suction. The title compound of formula

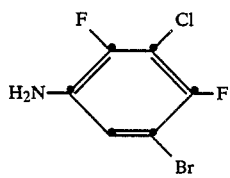

(Comp. no. 1.1.2.1.)

is obtained in the form of colourless crystals; m.p. 86°–88° C.

The following compounds are prepared in an analogous manner:

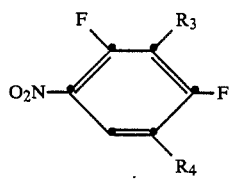

| Comp. no. | R$_3$ | R$_4$ | Physical data |
|---|---|---|---|
| 1.1.2.2. | Br | Cl | |
| | Br | Br | |

1.2. End products

1.2.1. N-(2,6-difluorobenzoyl)-N'-(2,4-difluoro-3-chloro-5-bromophenyl)-urea 3.75 g of 2,6-difluorobenzoyl isocyanate are added dropwise at room temperature, with stirring, to 5 g of 2,4-difluoro-3-chloro-5-bromoaniline dissolved in 50 ml of dry toluene, and the mixture is stirred for a further 5 hours. Approximately 75% of the solvent is then removed in a rotary evaporator. The residue is diluted with hexane and the resulting precipitate is filtered off with suction, washed with hexane and dried in vacuo. The title compound of formula

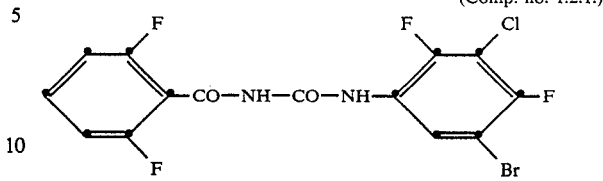

(Comp. no. 1.2.1.)

is obtained in the form of colourless crystals; m.p. 225°–227° C.

The following compounds are prepared in an analogous manner:

| Comp. no. | R | R$_1$ | R$_2$ | R$_3$ | R$_4$ | physical data |
|---|---|---|---|---|---|---|
| 1.2.2. | H | H | Cl | Cl | Br | m.p. 230–232° C. |
| 1.2.3. | F | F | F | Cl | Br | m.p. 220–221° C. |
| | H | F | F | Br | Cl | |
| | H | H | F | Cl | Br | |
| | H | F | Cl | Cl | Br | |
| | H | Cl | Cl | Cl | Br | |
| | H | F | OCH$_3$ | Cl | Br | |
| | H | OCH$_3$ | OCH$_3$ | Cl | Br | |
| | H | H | OCH$_3$ | Cl | Br | |
| | H | H | Cl | Br | Cl | |
| | H | H | F | Br | Cl | |
| | H | F | Cl | Br | Cl | |
| | H | Cl | Cl | Br | Cl | |
| | H | F | OCH$_3$ | Br | Cl | |
| | H | OCH$_3$ | OCH$_3$ | Br | Cl | |
| | H | H | OCH$_3$ | Br | Cl | |
| | F | F | F | Br | Cl | |
| | H | F | F | Br | Br | |
| | H | H | Cl | Br | Br | |

EXAMPLE 2

Formulations for active ingredients of formula I according to Preparation Example 1.2. (throughout, percentages are by weight)

| 2.1. Emulsifiable concentrates | (a) | (b) |
|---|---|---|
| a compound according to Preparation Example 1.2. | 10% | 25% |
| calcium dodecylbenzenesulfonate | — | 5% |
| castor oil polyethylene glycol ether (36 moles of ethylene oxide) | 25% | 5% |
| butanol | 15% | — |
| xylene mixture | — | 65% |
| ethyl acetate | 50% | — |

Emulsions of any desired concentration can be produced from such concentrates by dilution with water.

| 2.2. Solutions | (a) | (b) |
|---|---|---|
| a compound according to Preparation Example 1.2. | 10% | >5% |
| polyethylene glycol (mol. wt. 400) | 70% | — |

-continued

| 2.2. Solutions | (a) | (b) |
|---|---|---|
| N—methyl-2-pyrrolidone | 20% | 20% |
| epoxidised coconut oil | — | 1% |
| petroleum fraction (boiling range 160–190° C.) | — | 74% |

These solutions are suitable for application in the form of micro-drops.

| 2.3. Granulates | (a) | (b) |
|---|---|---|
| a compound according to Preparation Example 1.2. | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Extruder granulate | |
|---|---|
| a compound according to Preparation Example 1.2. | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.5. Coated granulate | |
|---|---|
| a compound according to Preparation Example 1.2. | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.6. Dusts | (a) | (b) | (c) | (d) |
|---|---|---|---|---|
| a compound according to Preparation Example 1.2. | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the active ingredient with the carriers and, if necessary, grinding the mixture in a suitable mill.

| 2.7. Wettable powders | (a) | (b) | (c) |
|---|---|---|---|
| a compound according to Preparation Example 1.2. | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |

-continued

| 2.7. Wettable powders | (a) | (b) | (c) |
|---|---|---|---|
| kaolin | 67% | 27% | — |

The active ingredient is thoroughly mixed with the adjuvants and the mixture is ground in a suitable mill, affording wettable powders which can be diluted with water to give suspensions of the desired concentration.

| 2.8. Suspension concentrate | |
|---|---|
| a compound according to Preparation Example 1.2. | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3

Biological tests 3.1. Action against *Musca domestica*

A sugar cube is moistened with a solution of the test compound in such a manner that the concentration of active ingredient in the cube after drying is 500 ppm. The treated cube is placed together with a wet cotton wool swab in a dish and covered with a beaker. 10 adult, one-week-old, OP resistant flies are placed beneath the beaker and kept at 25° C. and 50% humidity. After 24 hours the insecticidal action is determined by evaluating the mortality rate.

Compounds according to Example 1.2. exhibit good activity in this test.

3.2 Action against *Lucilia sericata*

1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds according to Example 1.2. exhibit good activity against *Lucilia sericata*.

3.3. Action against *Aedes aegypti*

A concentration of 12.5 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker. Mortality counts are made after 2 and 7 days.

Compounds according to Example 1.2. exhibit good activity in this test.

3.4. Insecticidal stomach poison action against *Spodoptera littoralis* larvae ($L_1$)

Cotton plants in the cotyledon stage are sprayed with an aqueous emulsion (obtained from a 10% emulsifiable concentrate) which contains 400 ppm of the test compound.

After the spray coating has dried, each cotton plant is populated with *Spodoptera littoralis* larvae in the $L_1$-stage. The test is carried out at 26° C. and about 50% relative humidity. The mortality is determined after 2 and 3 days, and after 5 days inhibition of the larvae's development and shedding is evaluated.

Compounds according to Example 1.2. exhibit 100% activity.

3.5 Insecticidal stomach poison action against *Spodoptera littoralis* and *Heliothis virescens* larvae ($L_3$)

Potted soybean plants (pot size: 10 cm diameter) in the 4-leaf stage are sprayed with aqueous emulsions which contain the test compound in a concentration of 0.75 ppm.

After two days, each treated soybean plant is populated with 10 larvae of *Spodoptera littoralis* and *Heliothis virescens* in the $L_3$-stage. The test is carried out at 26° C. and at about 60% relative humidity in dim light. After 2 and 5 days evaluation is made to determine the percentage mortality of the larvae.

Compounds according to Example 1.2. exhibit 80–100% activity (mortality) after 2 and 5 days in the case of Spodoptera and in the case of Heliothis.

3.6. Insecticidal stomach poison action against *Plutella xylostella* larvae ($L_2$)

Potted Chinese cabbage plants (pot size: 10 cm diameter) in the 4-leaf stage are sprayed with an aqueous emulsion which contains the test compound in a concentration of 0.75 ppm.

After 2 days the treated Chinese cabbage plants are populated with 10 *Plutella xylostella* larvae in the $L_2$-stage. The test is carried out at 26° C. and at about 60% relative humidity in dim light. After 2 and 5 days evaluation is made to determine the percentage mortality of the larvae.

Compounds according to Example 1.2. exhibit 80–100% activity (mortality) after 2 and 5 days.

3.7. Action against *Laspeyresia pomonella* (eggs)

Egg deposits of *Laspeyresia pomonella* which are not more than 24 hours old are immersed on filter paper in an acetonic-aqueous solution containing 400 ppm of the test compound for one minute. After the solution has dried, the filter paper and the eggs are placed in a petri dish and left at a temperature of 28° C. After 6 days the percentage hatch from the treated eggs is evaluated.

Compounds according to Example 1.2. exhibit good activity in this test.

3.8. Action against *Anthonomus grandis* (adults)

Two potted cotton plants in the 6-leaf stage are sprayed with aqueous wettable emulsion preparations containing 100 ppm of the test compound. After the spray coating has dried (about 1.5 hours), each plant is populated with 10 adult beetles (*Anthonomus grandis*). Plastic cylinders the upper openings of which are covered with gauze are then slipped over the treated plants populated with the test insects in order to prevent the beetles from migrating. The treated plants are kept at 25° C. and about 60% relative humidity. Evaluation is made after 2, 3, 4 and 5 days and is based on the percentage mortality of the test insects (% in dorsal position) and on the anti-feeding effect compared with untreated controls.

Compounds according to Example 1.2. exhibit good activity in this test.

3.9. Action against *Epilachna varivestis*

*Phaseolus vulgaris* plants (dwarf beans) about 15–20 cm in height are sprayed with aqueous emulsion preparations containing the test compound in a concentration of 800 ppm. After the spray coating has dried, each plant is populated with 5 larvae of *Epilachna varivestis* (Mexican bean beetle) is the $L_4$-stage. A plastic cylinder is slipped over the infested plants and covered with a copper gauze top. The test is carried out at 28° C. and 60% relative humidity.

The percentage mortality is determined after 2 and 3 days. Evaluation of feeding damage (anti-feeding effect) and of inhibition of development and shedding is made by observing the test insects for a further 3 days.

Compounds according to Example 1.2. exhibit good activity in this test.

3.10. Ovicidal action against *Heliothis virescens* and *Spodoptera littoralis*

Corresponding amounts of a wettable powder formulation containing 25% by weight of the test compound are mixed with sufficient water to produce an aqueous emulsion with an active ingredient concentration of 400 ppm.

One-day-old egg deposits of Heliothis on cellophane and of Spodoptera on paper are immersed in this solution for three minutes and then collected by suction on round filters. The treated deposits are placed in petri dishes and kept in the dark at 28° C. and 60% relative humidity. The hatching rate, i.e. the number of larvae which have developed from the treated eggs, in comparison with untreated controls, is determined after 5 to 8 days.

In this test, compounds according to Example 1.2. exhibit an 80–100% ovidical activity (mortality) against *Heliothis virescens* and *Spodoptera littoralis*.

What is claimed is:

1. Compounds of formula I

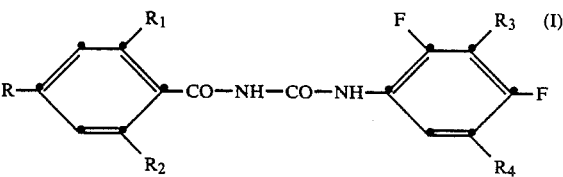

wherein R is hydrogen or fluorine; $R_1$ is hydrogen, fluorine, chlorine or methoxy; $R_2$ is fluorine, chlorine or methoxy; $R_3$ is bromine and $R_4$ is chlorine or bromine; or $R_3$ is chlorine and $R_4$ is bromine.

2. Compounds of formula I according to claim 1, wherein R is hydrogen; $R_1$ is hydrogen, fluorine or chlorine; $R_2$ is fluorine or chlorine; $R_3$ is bromine and $R_4$ is chlorine or bromine; or $R_3$ is chlorine and $R_4$ is bromine.

3. Compounds of formula I according to claim 2, wherein R is hydrogen; $R_1$ is hydrogen or fluorine; $R_2$ is fluorine or chlorine; $R_3$ is bromine and $R_4$ is chlorine; or $R_3$ is chlorine and $R_4$ is bromine.

4. Compounds according to claim 1 of formulae

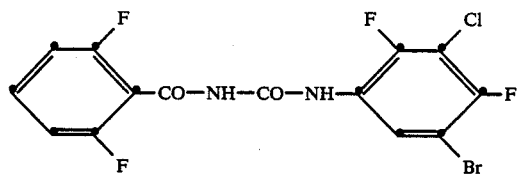

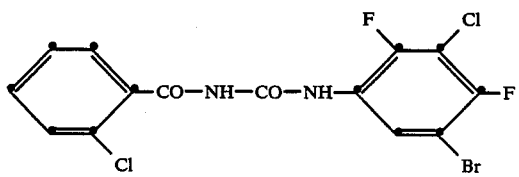

and

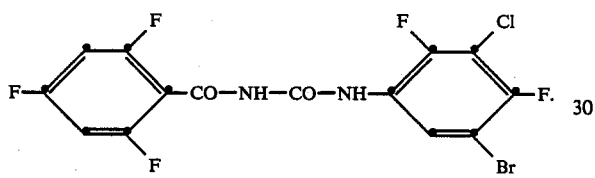

5. A pesticidal composition which contains as active ingredient a pesticidally effective amount of a compound of formula I

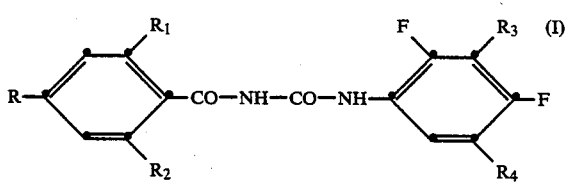

wherein R is hydrogen or fluorine; $R_1$ is hydrogen, fluorine, chlorine or methoxy; $R_2$ is fluorine, chlorine or methoxy; $R_3$ is bromine and $R_4$ is chlorine or bromine; or $R_3$ is chlorine and $R_4$ is bromine, together with suitable inert carriers and/or adjuvants that are tolerated by plants.

6. Compounds of formula II

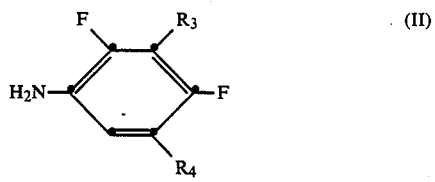

wherein $R_3$ is bromine and $R_4$ is chlorine or bromine, or $R_3$ is chlorine and $R_4$ is bromine.

7. The compound according to claim 6 of formula

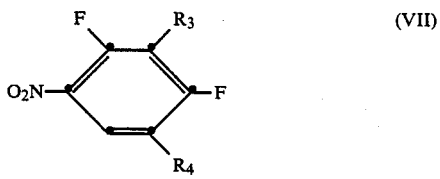

8. Compounds of formula VII

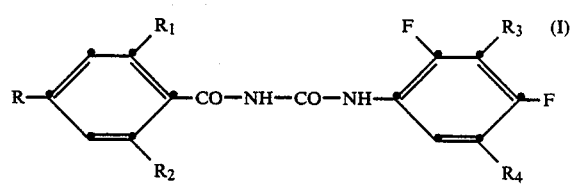

wherein $R_3$ is bromine and $R_4$ is chlorine or bromine, or $R_3$ is chlorine and $R_4$ is bromine.

9. The compound according to claim 8 of formula

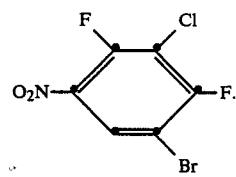

10. A method of controlling pests selected from insects and arachnids on animals and plants which comprises contacting said pests or their locus with a pesticidally effective amount of a compound of formula I

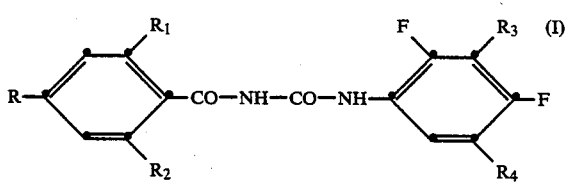

wherein R is hydrogen or fluorine; $R_1$ is hydrogen, fluorine, chlorine or methoxy; $R_2$ is fluorine, chlorine or methoxy; $R_3$ is bromine and $R_4$ is chlorine or bromine; or $R_3$ is chlorine and $R_4$ is bromine.

11. A method of use according to claim 10 for controlling larval stages of plant-destructive insects.

* * * * *